(12) United States Patent
Ross et al.

(10) Patent No.: US 7,758,498 B2
(45) Date of Patent: Jul. 20, 2010

(54) ENDOSCOPE WITH RELIEF OF AXIAL LOADING

(75) Inventors: Robert N. Ross, Gardner, MA (US); Richard E. Forkey, Westminster, MA (US)

(73) Assignee: Precision Optics Corporation, Gardner, MA (US)

( * ) Notice: Subject to any disclaimer, the term of this patent is extended or adjusted under 35 U.S.C. 154(b) by 601 days.

(21) Appl. No.: 11/161,945

(22) Filed: Aug. 23, 2005

(65) Prior Publication Data

US 2006/0004259 A1  Jan. 5, 2006

(51) Int. Cl.
*A61B 1/04* (2006.01)

(52) U.S. Cl. .................. 600/133; 600/101; 600/136; 600/138; 600/140; 600/176

(58) Field of Classification Search .......... 600/101, 600/133, 138
See application file for complete search history.

(56) References Cited

U.S. PATENT DOCUMENTS

| | | | |
|---|---|---|---|
| 4,036,218 A | 7/1977 | Yamashita et al. | 128/4 |
| 4,416,268 A | 11/1983 | Hagino | 128/6 |
| 4,895,138 A | 1/1990 | Yabe | 128/6 |
| 4,905,082 A | 2/1990 | Nishigaki et al. | 358/98 |
| 5,051,824 A | 9/1991 | Nishigaki | 358/98 |
| 5,156,142 A | 10/1992 | Anapliotis et al. | 128/6 |
| 5,601,525 A * | 2/1997 | Okada | 600/160 |
| 5,984,861 A | 11/1999 | Crowley | 600/175 |
| 6,095,970 A | 8/2000 | Hidaka et al. | 600/110 |
| 6,364,831 B1 | 4/2002 | Crowley | 600/175 |
| 6,419,628 B1 * | 7/2002 | Rudischhauser et al. | 600/161 |
| 6,569,087 B2 | 5/2003 | Naito et al. | 600/156 |
| 6,589,165 B2 | 7/2003 | Bodor et al. | 600/172 |
| 2003/0191366 A1 | 10/2003 | Ishibiki | 600/133 |

FOREIGN PATENT DOCUMENTS

| | | |
|---|---|---|
| EP | 0 044 018 A1 | 1/1982 |
| JP | 62-066220 | 3/1987 |
| JP | 05-154102 | 6/1993 |

OTHER PUBLICATIONS

Henke, Sass, Wolf- Mini-Rigid Borescopes, Specification Sheet.

* cited by examiner

*Primary Examiner*—Matthew J Kasztejna
(74) *Attorney, Agent, or Firm*—George A. Herbster

(57) ABSTRACT

A rigid endoscope includes an outer housing subassembly that supports an optics subassembly. The outer housing subassembly includes concentric tubes with optical fiber for providing object illumination. The optics subassembly includes a tubular sheath sealed at both ends for carrying lenses and other optical elements. First and second positioners associated with the optics subassembly and the outer housing subassembly, respectively, limit the transfer of axial forces from the proximal end of the endoscope to the tubular sheath.

11 Claims, 5 Drawing Sheets

ENDOSCOPE WITH RELIEF OF AXIAL LOADING

CROSS REFERENCE TO RELATED APPLICATION

Co-pending U.S. patent application Ser. No. 10/383,236 to Forkey et al. filed Mar. 6, 2003 now U.S. Pat. No. 6,955,644 granted Oct. 18, 2005 for an Autoclavable Endoscope, assigned to the same assignee as the present application; and Co-pending U.S. patent application Ser. No. 11/161,934 to Forkey et al. filed Aug. 23, 2005 for a Repairable Endoscope, assigned to the same assignee as the present application

FIELD OF THE INVENTION

This invention relates to endoscopes and more particularly to thin-walled endoscopes subject to damage from undue axial forces.

DESCRIPTION OF RELATED ART

Endoscopes come in two basic forms. In one form the endoscope is flexible. Optical fibers transfer an image from an optical objective to an eyepiece or other viewing device. The fibers produce image pixels of the image from the optical objective. Endoscopes of the second form are called rigid endoscopes. This invention is particularly applicable to rigid endoscopes. A rigid endoscope includes a tubular structure that carries an optical objective at a distal end and a relay lens system that transfers the image to a viewing device or eyepiece at a proximal end. Such devices typically provide better spatial resolution than flexible endoscopes do.

Recently several manufacturers have adopted a "tube-in-a-tube" design. With this design, all the lenses and other optical elements are positioned in a sealed tubular sheath as an optics subassembly. An outer housing subassembly includes a doubled walled structure with inner and outer tubes and intermediate optical fiber. The optical fiber conveys light from a source thereby to illuminate an object at the distal end of the endoscope. The inner tube forms a lumen or passage that receives the tubular sheath of the optics subassembly. An adhesive or epoxy fills some or all of the gap between the inner tube and the optics subassembly tubular sheath thereby to fix the two subassemblies relative to each other.

For example, U.S. Pat. No. 5,156,142 (1992) to Anapliotis et al. discloses an arthroscope with a shaft that carries an optical unit as part of an observation component and an illumination component. The illumination component includes a double-walled sheath that forms an annulus for carrying optical fibers and that forms a central passage. The observation component includes a lens formed with various channels about the periphery within a guidance tube to fit within the passage formed by the illumination component. As a result, the observation component can be removed from the arthroscope for repair.

U.S. Pat. No. 6,589,165 (2003) to Bodor et al. also describes an endoscope with a modular structure. The endoscope is characterized by having interchangeable image transmission systems. Should the optical components in the image transmission system fail, a mechanical latch is released. The damaged image transmission system can be removed from the endoscope for independent repair or replacement.

Endoscopes embodying the disclosure in U.S. Patent Publication No. US 2004-0176662 of Forkey et al. are characterized by including an inner optics assembly that is constructed with a tubular sheath that contains optical elements and is sealed at both ends to withstand the rigors of autoclaving. With this construction the sheath attaches at the distal end to an inner tube of an outer housing subassembly by an epoxy seal. The optics subassembly as shown in this reference comprises various lenses and other elements for forming an objective, a relay lens system and an eyepiece. Other designs, well known to those skilled in the art, can also be incorporated in an endoscope or like optical device.

In certain applications for each of these tube-in-a-tube constructions, it is important to minimize the outer diameter of the outer tube. One modification to existing designs for reducing the overall diameter is to reduce the thickness of various elements, such as the tubular sheath for the optics subassembly. However, in many devices the optics subassembly can be subjected to compression forces during construction, use and repair. As the tubular sheath wall becomes thinner, the possibility arises that these compressive forces will deform or warp the tubular sheath and thereby will degrade the viewed image.

If the distal end of an optics subassembly is fixed to the outer housing subassembly, as by a rigid epoxy, it is possible for differential thermal expansions to produce axial forces on the optics subassembly in either tension or compression upon heating, as during autoclaving. Such axial forces can also deform the tubular sheath.

What is needed is an endoscope that can benefit from all the advantages of a tube-in-a-tube construction design while minimizing the risk of damage due to the application of axial forces to the tubular sheath surrounding the lenses and other optical elements in an optics subassembly

SUMMARY

Therefore it is an object of this invention to provide an endoscope that incorporates a tube-in-a-tube construction with minimal risk of damage during repair and/or manufacture.

Another object of this invention is to provide an endoscope that incorporates a tube-in-a-tube construction to provide an endoscope that minimizes the risk of undue axial forces deforming a tubular sheath in an optics subassembly.

Yet another object of this invention is to provide an endoscope that incorporates a tube-in-a-tube construction to provide an endoscope that minimizes the risk of undue axial forces deforming an optics subassembly when the tubular sheath is thin.

Still another object of this invention is to provide an endoscope that is easy to manufacture and facilitates necessary adjustments during manufacture while minimizing the risk of deforming the tubular sheath of an optics subassembly.

In accordance with this invention, an endoscope having distal and proximal ends includes an outer housing subassembly with a lumen therethrough and an optics subassembly in said lumen including a tubular sheath. First and second positioners are associated with the optics housing subassembly and the outer housing subassembly, respectively. A fixing structure fixes the positioning structures thereby to prevent significant axial loading of the tubular sheath.

In accordance with another aspect of this invention an endoscope having distal and proximal ends comprises an outer housing subassembly and an optics subassembly. The outer housing subassembly has a central lumen therethrough. The optics subassembly lies in the lumen and includes a tubular sheath and a plurality of optical elements. The tubular sheath has sealed windows at each of the distal and proximal ends and extends through the central lumen. The plurality of optical elements in said tubular sheath forms an image of an object and presents the image for viewing. Material intermediate the outer housing subassembly and the tubular sheath prevent displacement therebetween during normal use. First and second positioning structures are associated with the optics subassembly and the outer housing subassembly, respectively. A structure fixes the positioning structures thereby to prevent significant axial loading of the tubular sheath.

In accordance with still another aspect of this invention an endoscope comprises an optics subassembly, an outer housing subassembly and an eyecup. The optics subassembly includes a tubular sheath having a predetermined cross section extending proximally from a distal end, a proximal collar attached to the proximal end of said tubular sheath, and optical lenses and elements carried in said tubular sheath. Optics in the tubular sheath present an image at the proximal end of said optics subassembly representing an object proximate the distal end of the optics subassembly. A first positioner at the proximal end of the collar establishes the axial position of the optics subassembly in said endoscope. The outer housing subassembly includes a body portion and an outer sheath attached to the body portion for forming a passage therethrough terminating at an open distal end for receiving the optics subassembly. The body portion includes a second positioner for engaging the first positioner thereby to define the position of the optics subassembly. The eyecup attaches to the proximal end of the body portion to apply an axial force to the first positioner thereby to fix the position of the optics subassembly with respect to the outer housing subassembly. Material intermediate the sheath and the outer sheath fixes at least the portions of the tubular sheath and the outer sheath over a portion extending proximally from the distal end.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
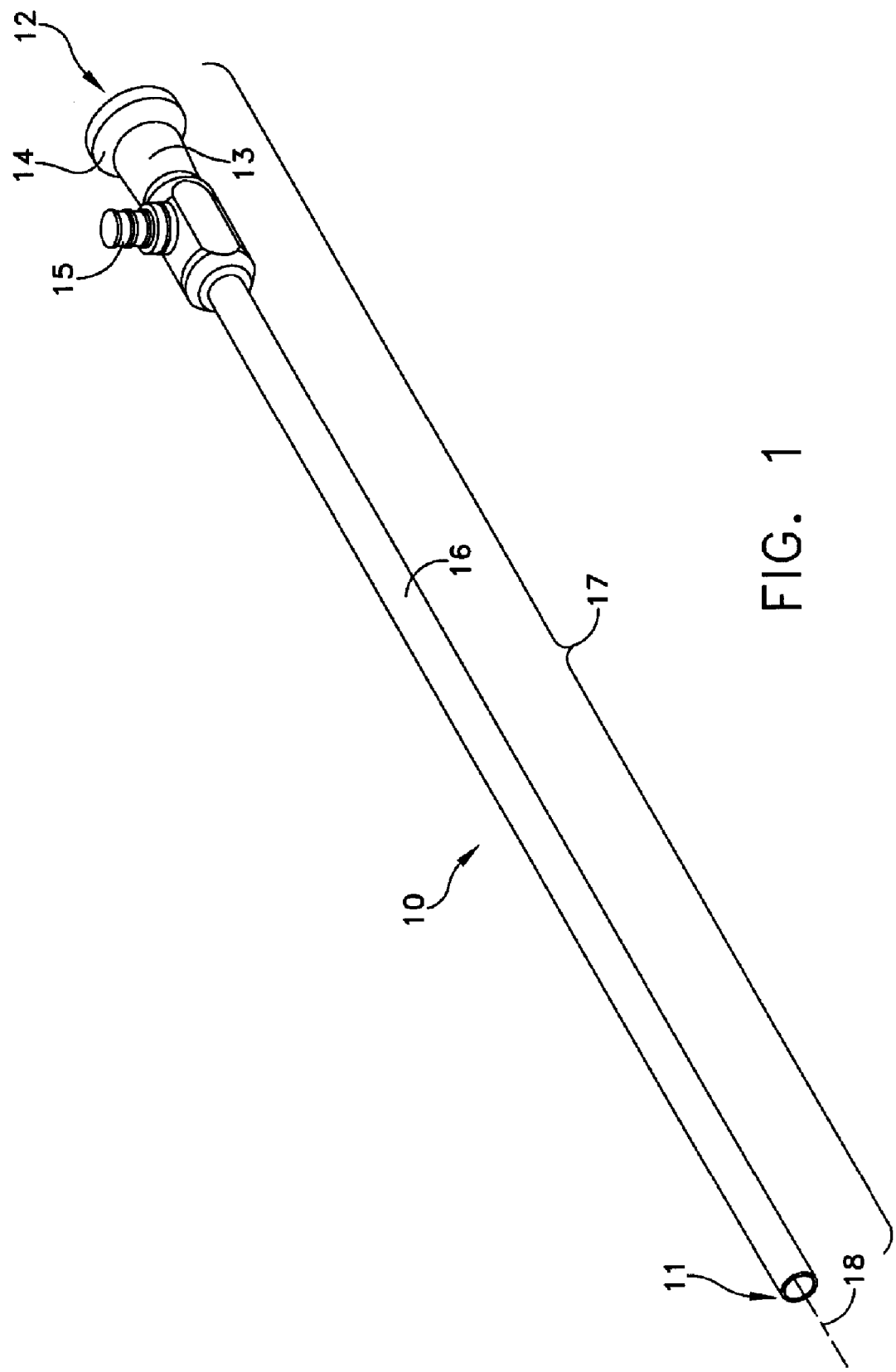
FIG. 1 is a perspective view of one embodiment of an endoscope constructed in accordance with this invention.

FIG. 1 depicts an endoscope 10 as it appears to medical personnel for use. It extends between a distal end 11, the end closest to the object to be imaged, and a proximal end 12, the end closest to the person using the device. This view depicts an optical body 13 with an eyecup 14 through which the image is viewed. A fiber post 15 receives an output connection from an illumination source thereby to provide light for transmission through optical fiber to illuminate the object being imaged. An outer sheath of a tube 16 extends from the optical body. All of these elements constitute components of an outer housing subassembly 17 that extends along an optical axis 18.

Figure 2:
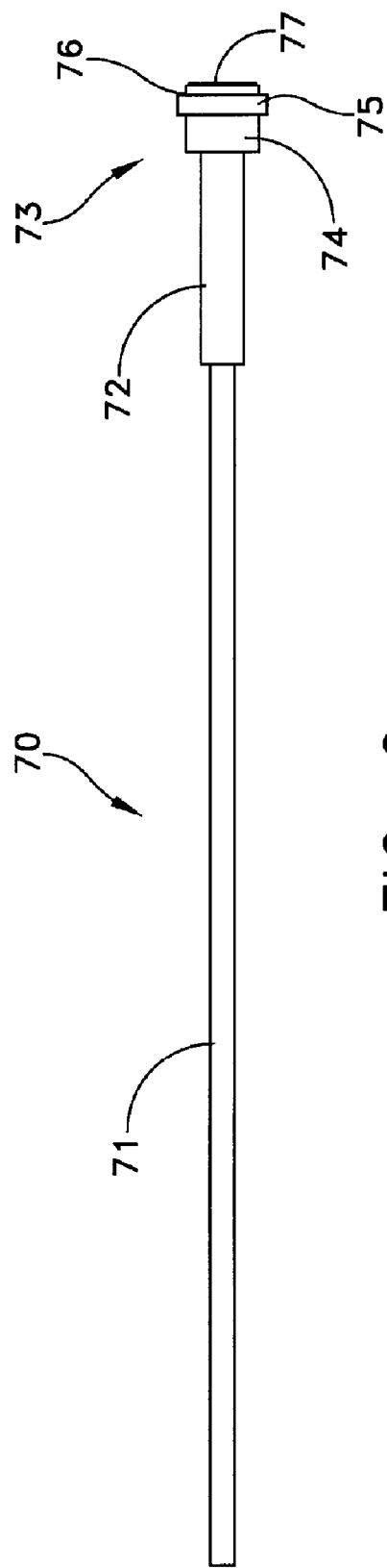
FIG. 2 is a plan view of an optics subassembly for use in the endoscope of FIG. 1.

The endoscope 10 houses an optics subassembly 70 as shown in FIG. 2. The optics subassembly 70 can have any of a variety of implementations. One such implementation is depicted in U.S. patent application Ser. No. 11/161,934. Consequently only the exterior of the sheath 71 and a collar 72 are disclosed in FIG. 2. The optics subassembly 70 includes a distal window (not shown) for sealing the distal end of the tubular sheath 71.

The collar 72 supports the proximal portion of the tubular sheath 71. At its proximal end the collar 72 carries a first positioning structure 73 including a distal shoulder 74, a circumferential and radially extending band 75 and a proximal shoulder 76. The proximal shoulder 76 circumscribes a proximal window 77. The proximal window 77 seals the optics subassembly 70 by being brazed or soldered to the proximal shoulder 76.

Figure 3:
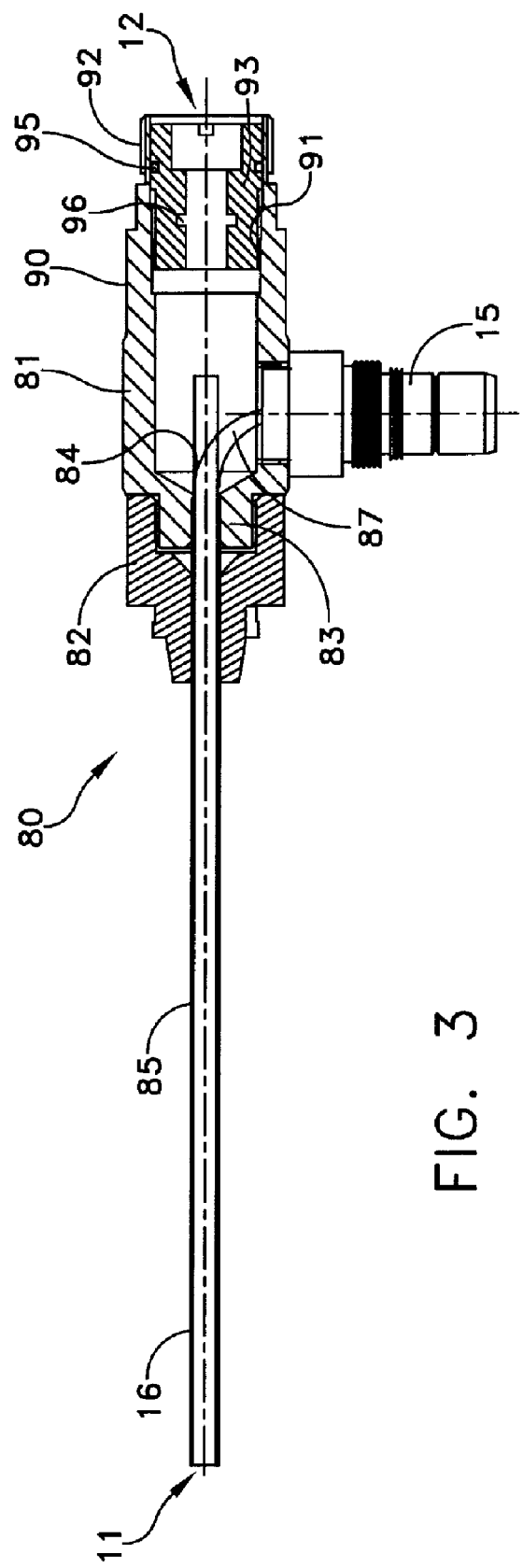
FIG. 3 is a sectional view of an outer housing subassembly for receiving the optics subassembly of FIG. 2.
Figure 4:
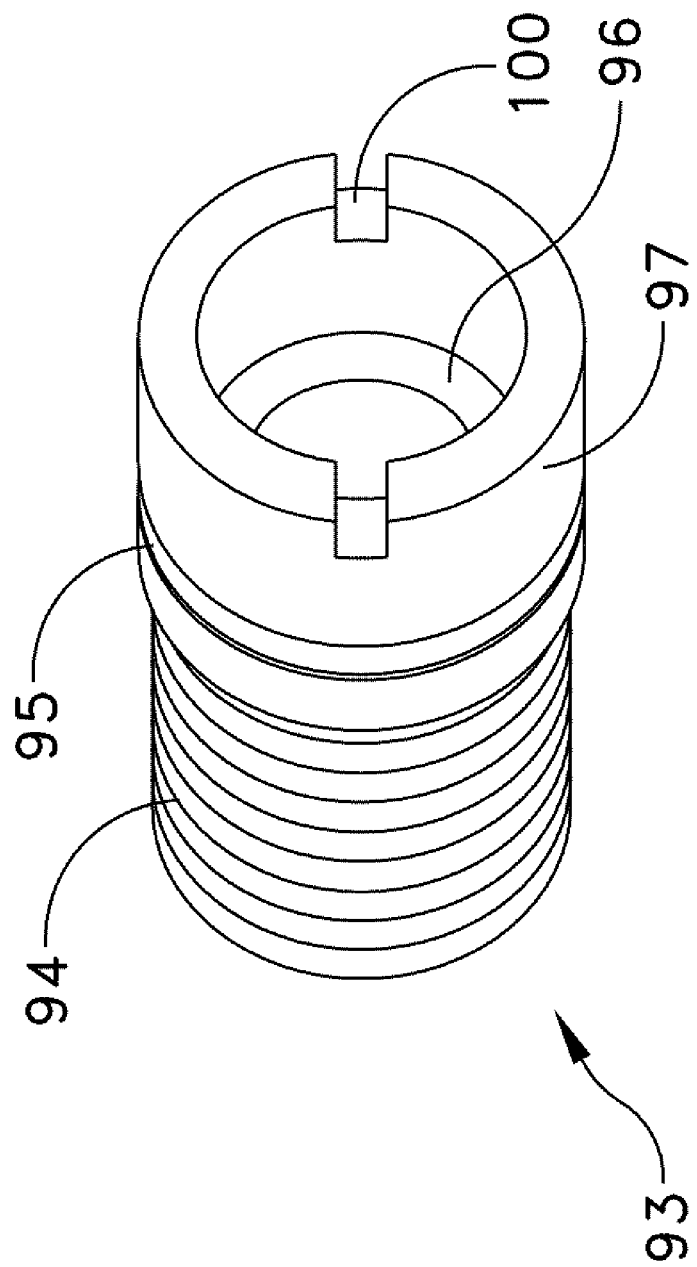
FIG. 4 is a perspective view of a positioner shown in the outer housing subassembly of FIG. 3.

FIGS. 3 and 4 depict an embodiment of an outer housing subassembly 80 that can receive the optics subassembly 70. As shown in FIG. 3, a proximal body 81 has an optional barrel adapter 82 attached to an end wall 83 with a central passage 84. The end wall 83 supports a double walled structure 85 within the proximal body 81. The outer wall of the structure 85 constitutes the outer sheath 16 in FIG. 1. The optical fiber post 15 carries optical fibers 87 which then are routed through the annular space between the inner and outer walls to extend to distal end 11 of the double walled structure 85.

Still referring to FIG. 3, the proximal body 81 includes a proximal extension 90 with internal threads 91 and external threads 92. As shown in FIG. 3 and more clearly in FIG. 4, a second positioning structure 93 has external threads 94 for engaging the internal threads 91. The second positioning structure 93 includes an external O-ring channel 95 for providing an O-ring seal between the second positioning structure 93 and the proximal extension 90. The second positioning structure 93 also has an internal O-ring channel 96 for providing a seal when the optics subassembly 70 is inserted in the outer housing subassembly 80. A proximal extension 97 of the second positioning structure 93 has diametrically opposite proximal axial slots 100.

Figure 5:
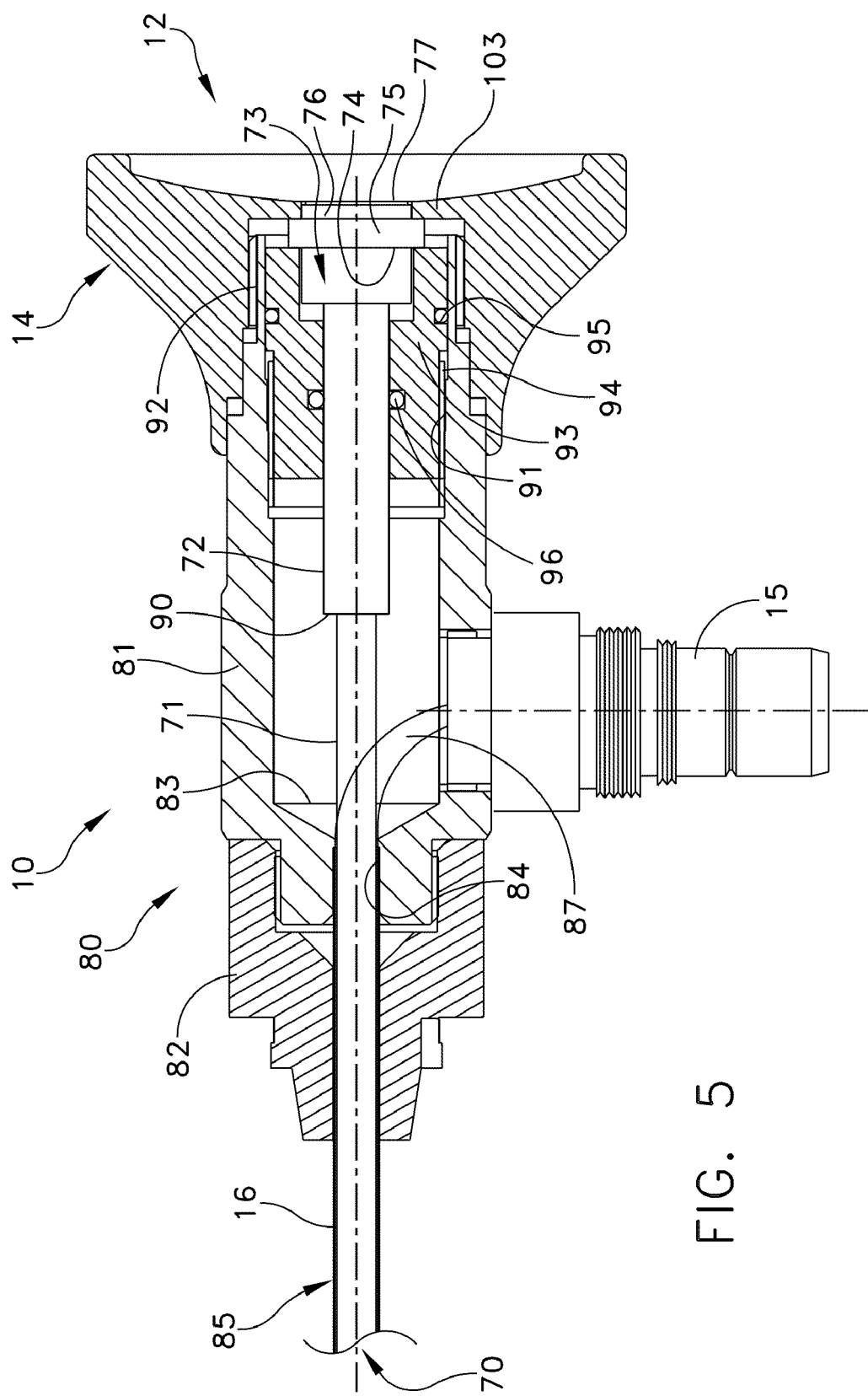
FIG. 5 is a sectional view of the proximal end of an endoscope with the subassemblies of FIGS. 2 and 3.

Referring to FIG. 5, during the construction of this particular embodiment of the endoscope 10, the outer housing subassembly 80 with the second positioning structure 93 removed will be positioned vertically in a fixture that blocks the open distal end 11. Then a predetermined amount of an epoxy or adhesive material, such as a Class VI silicone adhesive, will be introduced through the central passage 84 to fill the central lumen or passage of the double walled structure 85. Next the second positioning structure 93 will be threaded into the proximal body 81 thereby to constitute an adjustable stop that limits the distal position of the optics subassembly 70 in the outer housing subassembly 80. As a next step, the optics subassembly 70 is loaded into the outer housing subassembly 80 until the distal radial edge of the band 75 engages the proximal radial edge of the second positioning structure 93.

After removing any excess adhesive material, the eyecup 14 is threaded onto the external threads 92 until a central annular portion 103 engages the proximal radial edge of the band 75. Now the adhesive is allowed to cure.

As will now be apparent, the band 75 absorbs all the axial forces. No significant compressive forces are translated to the tubular sheath 71 so any potential for damage including misalignment due to compression of the tubular sheath 71 is essentially eliminated. In addition the second positioning structure 93 and the eyecup 14 stabilize the axial position of the optics subassembly 70 within the outer housing subassembly 80. Further, if the distal end of the optics subassembly is allowed to float axially, this structure prevents axial loading in tension or compression due to temperature changes.

As shown in FIG. 5, an endoscope has been constructed in accordance with this invention using the optics subassembly of FIG. 2 and the outer housing subassembly 80 of FIG. 3. Referring to both FIGS. 3 and 5, the double walled structure 85 has an outer diameter of 2.7 mm and a lumen of 2.20 mm. The sheath 71 has an outer diameter of 2.15 mm and an inner diameter of 2.05 mm, so the wall thickness of the tubular sheath 71 is 0.05 mm.

This structure can also facilitate repairs when the material intermediate the optics subassembly 70 and the outer housing 80 is an appropriate adhesive. Should repairs be required, the eyecup 14 in FIG. 5 is removed. Then a tool can be inserted to engage proximal axial slots 100, shown in FIG. 4, in the end of the second positioning structure 93. The second positioning structure 93 can then be unthreaded thereby advancing proximally or to the right in FIG. 5. This applies a force in tension to the tubular sheath 71 until the adhesive material tears and releases any withholding force on the optics subassembly 70. Then the optics subassembly 70 can be removed for repair.

After repair, the passage through the double walled structure 85 receives new adhesive. The position of the second positioning structure 93 can be reset. Then a new or replacement optics subassembly can be reinserted in the outer housing subassembly 80.

As will now be apparent, endoscopes, such as the endoscope 10 in FIGS. 1 and 5, constructed in accordance with this invention meet all the objectives of this invention. More specifically, the structure shown in FIGS. 2 through 5 provides an endoscope that is adapted for use with thin-walled and other structures where axial forces in compression or tension on an optics subassembly could have a deleterious effect.

Variations of the components constituting the disclosed endoscope have been discussed. A specific embodiment of the positioners has been shown. Other forms of these positioners can be substituted while attaining some or all of the advantages of this invention. It will be apparent that many other modifications could also be made to the disclosed apparatus without departing from the invention. Therefore, it is the intent of the appended claims to cover all such variations and modifications as come within the true spirit and scope of this invention.

What is claimed is:

1. An endoscope having distal and proximal end portions and comprising:
   A) an outer housing subassembly including:
      i) a first tubular sheath with a central passage therethrough, and
      ii) a proximal optical body attached to said first tubular sheath adjacent the proximal end with a central passage therethrough whereby said outer housing subassembly has open distal and proximal ends,
   B) an optics subassembly including:
      i) a second tubular sheath in said central passage intermediate said open distal end and said optical body,
      ii) optical elements including an objective lens system within said second tubular sheath, and
      iii) a first positioning structure fixed to said second tubular sheath adjacent the proximal end thereof with an external, circumferential band with proximal and distal radial edges,
   C) a second positioning structure with a proximal radial edge within said central passage for axial displacement therein adjacent the proximal end thereof, said outer housing subassembly and said second positioning structure including complementary means for adjusting the axial position of said second positioning structure relative to said outer housing subassembly whereby the engagement of said circumferential band distal radial edge and said second positioning structure proximal radial edge establishes the axial position of said optics subassembly in said outer housing subassembly, and
   D) an eyecup attached to the proximal end of said outer housing subassembly, said eyecup having a central annular portion for engaging said circumferential band proximal edge thereby fixing the axial position of said optics subassembly.

2. An endoscope as recited in claim 1 wherein said eyecup and said proximal end of said outer housing subassembly are threaded, said eyecup being threaded onto the proximal end of said outer housing subassembly until said central annular portion engages the proximal radial edge of said circumferential band.

3. An endoscope as recited in claim 1 wherein portions of the surface of said central passage and an outer surface of said second positioning structure have complementary threads thereby to provide the adjustment of the position of said second positioning structure in said central passage.

4. An endoscope as recited in claim 3 wherein said second positioning structure additionally includes means at the proximal end thereof for facilitating rotation of said second positioning structure within said outer housing subassembly.

5. An endoscope as recited in claim 4 wherein said rotation facilitation means includes a slot formed in said second positioning structure proximal end.

6. An endoscope having distal and proximal portions and comprising:
   A) an outer housing subassembly having a central passage extending between open distal and proximal ends and a proximally positioned optical body,
   B) an optics subassembly including:
      i) a tubular sheath having sealed windows at each of the distal and proximal ends, said tubular sheath being disposed in the central passage between the distal end and the optical body,
      ii) a plurality of optical elements including an objective lens system in said tubular sheath for forming an image of an object and presenting the image for viewing, and
      iii) a first positioning structure fixed to the periphery of said tubular sheath adjacent the proximal end thereof including an external, circumferential band and proximal and distal radial edges,
   C) adhesive material intermediate said outer housing subassembly and said tubular sheath and extending proximally from the distal end of said endoscope for preventing displacement between said outer housing and optics subassemblies during normal use,
   D) a second positioning structure with a proximal radial edge within said central passage for axial displacement therein adjacent the proximal end thereof, said second positioning structure including complementary means for establishing the axial position of said second positioning structure relative to said outer housing subassembly whereby engagement of said circumferential band radial edge and said second positioning structure proximal radial edge establishes the axial position of said optics subassembly in said outer housing subassembly, and E) an eyecup attached to the proximal end of said outer housing subassembly, said eyecup having a central annular portion for engaging said circumferential band proximal edge thereby fixing the axial position of said optics subassembly.

7. An endoscope as recited in claim 6 wherein said eyecup and said proximal end of said outer housing subassembly are threaded, said eyecup being threaded onto the proximal end of said outer housing subassembly until said central annular portion engages the proximal radial edge of said circumferential band.

8. An endoscope as recited in claim 7 wherein portions of the surface of said central passage and an outer surface of said second positioning structure have complementary threads thereby to provide the adjustment of the position of said second positioning structure in said central passage.

9. An endoscope as recited in claim 6 wherein said second positioning structure additionally includes means at the proximal end thereof for facilitating rotation of said second positioning structure within said outer housing subassembly.

10. An endoscope as recited in claim 9 wherein said rotation facilitation means includes an slot formed in said second positioning structure proximal end.

11. A repairable, autoclavable endoscope comprising:
A) an optics subassembly including:
  i) a sheath having a predetermined cross section extending proximally from a distal end,
  ii) a proximal collar attached to the proximal end of said tubular sheath,
  iii) optical means including an optical objective sealed in said tubular sheath for presenting an image at the proximal end of said optics subassembly representing an object proximate the distal end of said optics subassembly, and
  iv) first positioning means on said proximal collar having proximal and distal radial edges for defining an axial stop position for said optics subassembly,
B) an outer housing subassembly including:
  i) a optical body portion, and
  ii) outer sheath means attached to said body portion for forming a central passage extending through and terminating at open distal and proximal ends, said optics subassembly being located in the central passage,
C) second positioning means adjacent the proximal end of, and axially adjustable within, said outer housing subassembly thereof including a proximal radial edge for defining an axial position for said optics subassembly,
D) eyecup means for attachment to the proximal end of said body portion to engage said first positioning means proximal radial edge thereby, with the proximal edge of said second positioning means, capturing said optics subassembly at a final axial position, and
E) material intermediate said sheaths of said optics and outer housing subassemblies for fixing the positions thereof proximate the distal end of said endoscope.

* * * * *